United States Patent [19]
Lumma

[11] 4,242,344
[45] Dec. 30, 1980

[54] PIPERAZINYL-IMIDAZO[1,2-A]PYRAZINES

[75] Inventor: William C. Lumma, Pennsburg, Pa.

[73] Assignee: Merck & Co., Inc., Rahway, N.J.

[21] Appl. No.: 73,574

[22] Filed: Sep. 7, 1979

Related U.S. Application Data

[63] Continuation-in-part of Ser. No. 4,970, Jan. 22, 1979.

[51] Int. Cl.$^3$ .................. A61K 31/495; C07D 401/14; C07D 403/14
[52] U.S. Cl. .................................... 424/251; 544/346; 544/350; 544/358; 544/382
[58] Field of Search ................. 544/350, 346; 424/251

[56] References Cited

U.S. PATENT DOCUMENTS

| | | | |
|---|---|---|---|
| 3,594,479 | 7/1971 | Maquire et al. | 544/350 |
| 3,973,017 | 8/1976 | Anderson | 544/350 |
| 4,082,845 | 4/1978 | Saari et al. | 544/350 |

OTHER PUBLICATIONS

DePompei et al., "J. Heterocyclic Chem.", vol. 12, (1975), pp. 861–863.
Lednicer et al., *The Organic Chemistry of Drug Synthesis*, 1977, John Wiley and Sons, New York, pp. 277–280.
Weissberger et al., *Special Topics in Heterocyclic Chem.*, 1977, John Wiley and Sons, New York, pp. 11–13, 23, 183–186, 211–213.

*Primary Examiner*—Donald G. Daus
*Assistant Examiner*—James H. Turnipseed
*Attorney, Agent, or Firm*—Mario A. Monaco; William H. Nicholson

[57] ABSTRACT

Piperazinyl-imidazo[1,2-a]pyrazines, derived from reactions between halo-imidazo[1,2-a]pyrazines with piperazine derivatives, are found to be active anorexic, antidepressant, antihypertensive, analgesic, antiarrhythmic, and/or anti-smoking agents.

9 Claims, No Drawings

PIPERAZINYL-IMIDAZO[1,2-A]PYRAZINES

This is a continuation-in-part of Ser. No. 004,970, filed Jan. 22, 1979.

BACKGROUND OF THE INVENTION

Only a few substituted imidazo[1,2-a]pyrazines are known. The parent imidazo[1,2-a]pyrazine has been prepared only recently, in substantial yield (39.2%), by DePompei et al., *J. Het. Chem.* 12, 86 (1975).

Employing a modification of this procedure which condenses aminopyrazines with α-halo carbonyl compounds prepared in situ from their diethylacetals, and newly developed methods involving condensation between a dihalopyrazine and an α-hydroxy-alkylamine or a propargyl amine, a number of novel imidazo[1,2-a]pyrazines have been prepared and converted to piperazinyl-imidazo[1,2-a]pyrazines.

These compounds are found to be 5-hydroxytryptamine agonists or reuptake blockers, and accordingly show anorexic, antidepressant, antihypertensive and/or analgesic activity. They are also β-blockers and are accordingly antiarrhythmic agents. In addition the compounds block the self-administration of nicotine in laboratory animals and are thus antismoking agents.

Therefore it is an object of this invention to provide novel piperazinylimidazo[1,2-a]pyrazines with anorexic, antidepressant, antihypertensive, analgesic, antiarrhythmic, and/or antismoking activities. It is also an object of this invention to provide procedures for preparing these novel compounds.

Another object is to provide pharmaceutical formulations for the administration of these novel compounds.

A further object is to provide a method of producing an anorexic, antidepressant, antihypertensive, analgesic, antiarrhythmic, and/or anti-smoking effect in a mammalian (human or animal) patient in need of such treatment.

DETAILED DESCRIPTION OF THE INVENTION

The novel and pharmaceutically valuable compound of this invention has the structural formula:

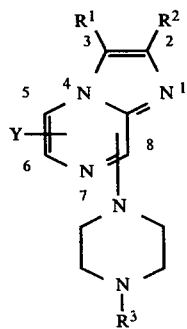

or pharmaceutically acceptable salt thereof, wherein: the piperazinyl group

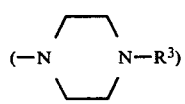

and Y are at positions 5, 6 or 8;
$R^1$ and $R^2$ independently are
- (a) hydrogen;
- (b) lower alkyl especially $C_{1-6}$ alkyl such as $-CH_3$, $-C_3H_7$, $-C_4H_9$ or $-C_6H_{13}$;
- (c) lower cycloalkyl especially $C_{3-6}$ cycloalkyl, such as cyclopropyl, cyclopentyl or cyclohexyl;
- (d) lower alkylthio especially $C_{1-3}$ alkylthio such as $CH_3S-$, $C_2H_5S-$ or $C_3H_7S-$;
- (e) halo such as F, Cl, Br or I;
- (f) $-CF_3$;
- (g) $CF_3S-$;
- (h) $C_6H_5-$;
- (i) phenyl-substituted by halogen such as $C_6H_4Cl-$; $C_6H_3F_2-$; $C_6H_4I-$; $C_6H_3FCl-$;
- (j) phenyl-substituted by $C_{1-3}$ alkyl such as $CH_3-C_6H_4-$; $C_3H_7-C_6H_4-$;
- (k) phenyl-substituted by $C_{1-3}$ alkoxy such as $CH_3O-C_6H_4-$;
- (l)

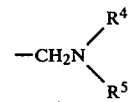

wherein $R^4$ is hydrogen or $C_{1-6}$ alkyl and $R^5$ is $C_{1-6}$ alkyl or $R^4$ and $R^5$ joined together form, with the nitrogen atom to which they are attached, a 5 or 6 membered heterocyclic group such as a piperidino group;
- (m)

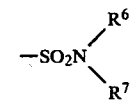

wherein $R^6$ and $R^7$ are independently hydrogen, $C_{1-3}$ alkyl, or phenyl;
$R^1$ and $R^2$ joined together represent $-CH_2CH_2CH_2-$ or $-CH_2CH_2CH_2CH_2-$;
$R^3$ is
- (a) hydrogen;
- (b) lower alkyl especially $C_{1-3}$ alkyl;
- (c) lower(cycloalkyl-alkyl) especially $C_{4-10}$(cycloalkyl-alkyl) such as cyclopropylmethyl, cyclopentylethyl or cyclohexylbutyl;
- (d) lower cycloalkyl especially $C_{3-6}$ cycloalkyl such as cyclopropyl, cyclopentyl or cyclohexyl;
- (e) lower alkanoyl especially $C_{1-6}$ alkanoyl such as

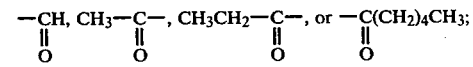

and
Y is
- (a) hydrogen;
- (b) halo such as F, Cl, Br, or I;
- (c) $-C\equiv N$;
- (d) $-CF_3$;
- (e) lower alkyl especially $C_{1-6}$ alkyl such as $-CH_3$, $-C_3H_7$ or $-C_5H_{11}$; or
- (f) lower alkoxy especially $C_{1-3}$ alkoxy such as $-CH_3O-$, $C_2H_5O-$, or $C_3H_7O$;
- (g) $-COOH$.

The piperazinyl group, as well as Y is preferably attached at position 6 or 8. However, the more preferred position for the piperazinyl group is at 8 and for Y it is at 6.

It is preferred that $R^1$ and $R^2$ are independently
(a) hydrogen;
(b) halo;
(c) $CF_3$;
(d) $CF_3S$;
(e) $C_6H_5$;
(f) phenyl-substituted by halogen;
(g)

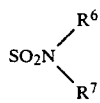

(h)

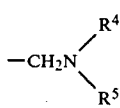

that $R^1$ and $R^2$ are joined together to form $-CH_2CH_2CH_2-$ or $-CH_2CH_2CH_2CH_2-$.

More preferably, $R^1$ and $R^2$ are independently
(a) hydrogen;
(b) Cl, Br or F;
(c) $CF_3$;
(d) $CF_3S$;
(e) o-Cl—$C_6H_4$—;
(f) —$SO_2N(CH_3)_2$;
(g)

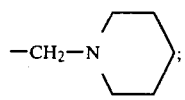

or
where $R^1$ and $R^2$ are joined together they form $-CH_2CH_2CH_2CH_2-$.

$R^3$ is preferably
(a) hydrogen;
(b) $C_{1-3}$ alkyl such as —$CH_3$, —$C_2H_5$— or —$C_3H_7$—;
(c) $C_{1-3}$ alkanoyl such as

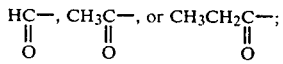

(d) cyclopropylmethyl; or
(e) cyclopropyl or cyclohexyl.

More preferably, $R^3$ is
(a) hydrogen;
(b) —$CH_3$; or
(c) cyclopropylmethyl; and Y is preferably
(a) hydrogen;
(b) Cl, F, Br or I;
(c) —C≡N;
(d) —$CF_3$; or
(e) $CH_3O$—.

More preferably Y is
(a) hydrogen; or
(b) Cl, F, or Br.

The most preferred embodiments of this invention are:
(a) wherein the piperazinyl group is at position 8; Y is at position 6; $R^1$ and $R^2$ are independently hydrogen or Cl; $R^3$ is hydrogen or —$CH_3$—; and Y is hydrogen or Cl; and
(b) 3-chloro-6-(1-piperazinyl)imidazo[1,2-a]pyrazine.

As the novel compounds of this invention are organic bases, their pharmaceutically acceptable salts are those resulting from the neutralization of the base with an acid. The acid employed is usually an inorganic acid such as a hydrohalic acid such as hydrochloric or hydrobromic acid; sulfuric acid; nitric acid; or phosphoric acid. An organic acid such as maleic, fumaric, tartaric, citric, acetic, salicyclic, succinic, benzoic, benzenesulfonic, glutamic, lactic or isethionic acid is also commonly used. Generally the neutralization is conducted in an inert solvent such as water; a $C_{1-3}$ alkanol such as methanol, ethanol or isopropanol; a $C_{3-6}$-ketone such as acetone, or ethylmethyl ketone; an ethereal solvent such as diethyl ether, tetrahydrofuran or dioxane; acetonitrile; or an aromatic solvent such as toluene. Mixtures of the above described solvents are also employed. Generally the neutralization is carried out in aqueous ethanol, at 0°–75° C., preferably at 0°–25° C., followed by filtration to collect the salts.

The novel compounds of this invention are prepared by a process comprising treating a substituted imidazo[1,2-a]pyrazine of the structural formula (II):

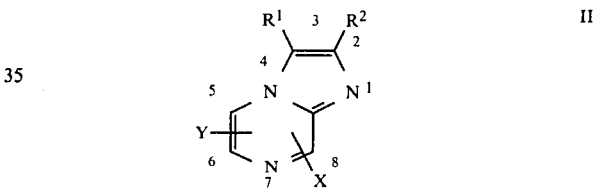

wherein:
X and Y are at positions 5, 6 or 8;
$R^1$ and $R^2$ and Y are as previously defined; and
X is halo such as chloro, bromo, iodo or fluoro;
with a piperazine of the structural formula:

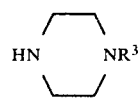

wherein $R^3$ is as previously defined.

The reaction is usually carried out in an inert solvent such as acetonitrile; a $C_{1-4}$ alkanol such as methanol, ethanol, n-propanol, or t-butanol; a fluoro-$C_{1-4}$ alkanol such as 2,2,2-trifluoroethanol, or perfluorobutanol; a chloro $C_{1-4}$ alkane such as methylene chloride, chloroform or 1,2-dichloroethane; or an ether such as diethyl ether, tetrahydrofuran or 1,2-dimethoxyethane; or a mixture of thereof.

Generally, the reaction mixture is maintained at about 5°–100° C., preferably at about 20°–30° C., until reaction is substantially complete, usually about 15 minutes to 48 hours, preferably 30 minutes to 24 hours.

The starting materials in the preparation of the novel compounds of this invention are the substituted imidazo[1,2-a]pyrazines of formula (II). They are preparable from 2-aminopyrazines by the following methods as shown below in Routes (a)–(e):

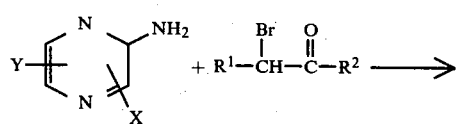

(a)

(III)

(II)

(b)

III + BrCH₂—C(=O)—R² ⟶

[R¹] ⟶ (II)

III + BrCH—CHO (R¹) ⟶   (c)

[R²] ⟶ (II)

wherein,

X is Cl, Br, I or F; and

[R¹] and [R²] each represents one of the following active electrophilic groups;

(1) halo (Cl, Br, I, F) derived from a halogenating reagent such as N-chlorosuccinimide, N-bromosuccinimide, Cl₂, Br₂, I₂, t-butylhypochlorite or perchlorylfluoride;

(2) lower alkylthio (CH₃S, C₂H₅S or C₃H₇S) or CF₃S derived from the corresponding sulfenyl chloride;

(3)

—SO₂N(R⁶)(R⁷)

derived from chlorsulfonic acid followed by amination; or (4)

—CH₂N(R⁴)(R⁵)

derived from formaldehyde and an amine.

(IV) + R¹CHCH NH₂ (OH) ⟶   (d)

(IVa)

[O] ↓

(IV bₐ)

[R²] ⟶

(IVb)

−H₂O ↓

II (e)

(IV) —Rₐ¹G≡CCH₂NH₂⟶

(V) —H₂O/CF₃COOH or NaOEt/EtOH⟶ (II)

Rₐ¹ is hydrogen, lower alkyl, phenyl, halophenyl, C₁₋₃ alkylphenyl, or C₁₋₃ alkoxyphenyl.

Routes (a), (b) and (c) involve the most commonly used method for the synthesis of 1,2-fused imidazoles by alkylating a substituted 2-aminopyrazine with an α-halocarbonyl compound to form a salt with the 1-pyrazinyl nitrogen, which in turn cyclizes on heating or treatment with a dehydrating agent such as trifluoroacetic anhydride to afford a substituted imidazo[1,2-a]pyrazine (II). In Route (b) and (c), $R^1$ and $R^2$ are introduced respectively via electrophilic substitution to give compound (II) inaccessible by Route (a).

On the other hand, Route (d) involves the nucleophilic displacement of the 2-halogen in a 2-halopyrazine followed by subsequent oxidation and cyclization to afford (II). Following Route (d), a substituted 2-halopyrazine of the structural formula IV wherein X and Y are independently at position 3, 5 or 6; X and Y are as previously defined in Formula (I); and Z is halo such as chloro, bromo, iodo, or fluoro, is treated with a β-hydroxy-alkylamine of the structural formula:

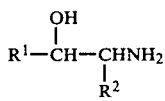

wherein $R^1$ and $R^2$ are as previously defined in formula (I) in an inert, polar solvent such as dioxane, N,N-dimethylformamide, hexamethylphosphoramide, tetrahydrofuran, 1,2-dimethoxyethane, pyridine, or bis-(2-methoxyethyl)ether, preferably dioxane, at 25°–150° C., preferably 90°–120°, until the reaction is substantially complete, usually 6–48 hours, preferably 12–24 hours. The resulting 2-amino derivative, (IVa), is then treated with a selective oxidation reagent such as trimethylamine-sulfur trioxide complex in dimethylsulfoxide containing triethylamine at 10°–45° C., preferably at 20°–30° C., until reaction is substantially complete, usually 6–24 hours, preferably 15–18 hours, to afford the corresponding α-keto derivative (IVb). This in turn is cyclized by treatment with a condensation reagent such as trifluoroacetic, trichloroacetic, or acetic anhydride in an acid such as trifluoroacetic, trichloroacetic, chloroacetic or acetic acid, with the preferred combination being that of trifluoroacetic anhydride in trifluoroacetic acid, at 10°–50° C., preferably at 20°–30° C., until the condensation is substantially complete in about 10 minutes to about 3 hours, preferably 20 minutes to about 1 hour.

The last procedure, Route (e), involves the nucleophilic substitution of a 2-halopyrazine by propargylamine followed by the mercuric oxide catalyzed cyclocondensation in trifluoroacetic acid to give compound (II).

A novel method of treatment, involving the novel piperazinyl-imidazo[1,2-a]pyrazines of this invention, comprises the administration of an active compound, for example, 3-chloro-6-(1-piperazinyl)imidazo[1,2-a]pyrazine, as an anorexic agent to a mammalian species, e.g. rats, rabbits, or human patients in amounts ranging from about 0.01 to about 20 mg per kg of body weight, preferably from about 0.1 to about 10 mg per kg of body weight in a single dose or in 2 to 4 divided doses.

These compounds in the described dosages are preferably administered orally; however, they can also be administered intraperitoneally, subcutaneously, intramuscularly or intravenously. For example, for oral therapeutic administration, an active compound of this invention is usually incorporated with excipients and used in the form of tablets, troches, capsules, elixirs, suspensions, syrups, wafers, chewing gum, and the like. The amount of an active compound in such a therapeutically useful composition or preparation usually ranges from 1 to 500 mg, preferably 5–250 mg, per unit dosage.

The previously described tablets, troches, capsules, pills and the like usually contain one or more of the following inactive ingredients: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin and/or a flavoring agent such as peppermint, oil of wintergreen, or cherry flavoring may be added. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

In addition to the anorexic activity described above, the novel compounds of this invention, for example, 3-chloro-8-(1-piperazinyl)imidazo[1,2-a]pyrazine and 6-chloro-8-(1-piperazinyl)imidazo[1,2-a]pyrazine, are pharmacologically active in regulating central serotonin levels in a manner suggesting that they are also useful as potential antidepressant, antihypertensive, analgesic and sleep-inducing agents. For these usages, essentially the same doses and routes of administration as well as the pharmacological formulations as described previously are employed.

The novel compounds of this invention are also β-blockers and show the usual effects of β-blockade and are thus useful as antiarrhythmic agents. Essentially the same dosages, formulations and routes of administration described above are employed for this utility.

The novel compounds also have the property of inhibiting the self-administration of nicotine in laboratory animals and thus have utility as anti-smoking agents. Again the dose levels, formulations and routes of administration are as previously described.

EXAMPLE 1

6-Chloro-8-(1-piperazinyl)imidazo[1,2-a]pyrazine

Step A: Preparation of 8-bromo-6-chloroimidazo[1,2-a]pyrazine

A mixture of bromoacetaldehyde diethylacetal (6.2 g), water (2 ml) and 40% aqueous hydrobromic acid (2 ml) is refluxed for 1.5 hours under nitrogen. The mixture is cooled, diluted with 100 ml of isopropanol, treated with sodium bicarbonate (16 g) and filtered to give a solution of bromoacetaldehyde which is treated with 3-bromo-5-chloro-2-aminopyrazine (4.17 g, 0.020 mol) at reflux for 18 hours under nitrogen. The mixture is concentrated to one-third the volume under vacuum, and treated with 4 ml of 40% aqueous hydrobromic acid. Fresh isopropanol is added and the resulting mixture is reconcentrated to give 6 g of the crude hydrobromide salt of the product. The crude salt is partitioned between aqueous sodium carbonate and chloroform; the resulting chloroform extract is treated with charcoal, filtered through diatomaceous earth, concentrated under vacuum, and sublimed to afford crystalline 8-bromo-6-chloroimidazo[1,2-a]pyrazine, m.p. 146°-147° C.

Employing the procedure substantially as described in Example 1, Step A, but substituting for the bromoacetaldehyde used therein, a similar stoichiometric amount of each of the α-bromocarbonyl compounds listed below in Table I, there is obtained in each case the corresponding imidazo[1,2-a]pyrazine also listed in Table I:

TABLE 1

| α-Bromo-carbonyl compounds | Derivatives of imidazo-[1,2-a]pyrazines |
|---|---|
| 2-bromocyclohexanone | 8-bromo-2,3-butano-6-chloroimidazo[1,2-a]-pyrazines (m.p. 142–157° C.) |
| 1-bromo-3,3,3-trifluoro-2-propanone | mixture of 95% 8-bromo-6-chloro-2-trifluoro-methylimidazo[1,2-a]-pyrazine and 5% of its 8-chloro analog |
| 1-(o-chlorophenyl)-2-bromo-1-ethanone | 8-bromo-6-chloro-2-(o-chlorophenyl)imidazo-[1,2-a]pyrazine |
| 1-bromo-1-cyclopropyl-2-butanone | 8-bromo-6-chloro-3-cyclopropyl-2-ethylimidazo-[1,2-a]pyrazine |
| bromocyclopropylmethyl-acetaldehyde | 8-bromo-6-chloro-3-cyclopropylmethylimidazo-[1,2-a]pyrazine |
| 1-bromo-1-phenyl-2-propanone | 8-bromo-6-chloro-2-methyl-3-phenylimidazo-[1,2-a]pyrazine |
| 1-(m-methoxy phenyl)-2-bromo-1-ethanone | 8-bromo-6-chloro-2-(m-methoxy phenyl)imidazo[1,2-a]pyrazine |
| 1-bromo-1-(p-tolyl)-2-pentanone | 8-bromo-6-chloro-2-propyl-3-(p-tolyl)-imidazo[1,2-a]pyrazine |

Similarly, employing the procedure substantially as described in Example 1, Step A, but substituting for the 3-bromo-5-chloro-2-aminopyrazine used therein, a similar stoichiometric amount of each of the aminopyrazines listed in Table II, there is obtained in each case the corresponding imidazo[1,2-a]pyrazine, also listed in Table II:

TABLE II

| Substituted aminopyrazines | Derivatives of imidazo-[1,2-a]pyrazines |
|---|---|
| 3-chloro-2-aminopyrazine | mixture of 8-chloro and 8-bromoimidazo[1,2-a]-pyrazines (m.p. 176–178° C.) |
| 2-chloro-5-aminopyrazine | 6-chloroimidazo[1,2-a]-pyrazine (m.p. 137–138° C.) |
| 2-chloro-6-aminopyrazine | 5-chloroimidazo[1,2-a]-pyrazine (m.p. 95–95.5° C.) |

Step B: Preparation of 6-chloro-8-(1-piperazinyl)imidazo[1,2-a]pyrazine dihydrochloride A mixture of 2.32 g (0.010 mole) of 8-bromo-6-chloroimidazo[1,2-a]pyrazine and an excess amount of piperazine (3 g) in 25 ml of acetonitrile is refluxed for 24 hours under nitrogen. It is then concentrated in vacuo and the resulting residue partitioned between water and methylene chloride. The methylene chloride extract is washed with three volumes of a 1 N aqueous solution of sodium hydroxide, dried over anhydrous sodium sulfate, and concentrated in vacuo to an oil which is purified by chromatography on silica gel. Elution with 10% methanol-chloroform gives the pure base which is treated with an ethanolic solution of hydrogen chloride to give the hydrochloride salt. Recrystallization from aqueous ethanol gives pure 6-chloro-8-(1-piperazinyl)imidazo[1,2-a]pyrazine di(hydrochloride)salt, m.p. >350° C.

Employing the procedure substantially as described in Example 1, Step B, but substituting for the 8-bromo-6-chloroimidazo[1,2-a]pyrazine and the piperazine used therein, the imidazo[1,2-a]pyrazines and piperazines described in Table III, there are produced the corresponding piperazinylimidazo[1,2-a]pyrazines, also described in Table III, in accordance with the following reaction:

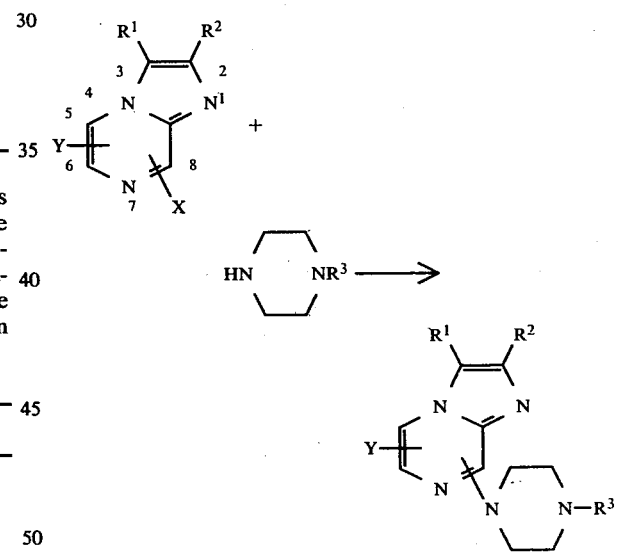

TABLE III

| Cpd. No. | R¹ | R² | X | n$_{xp}$* | Y | n$_y$** | R³ | m.p. of salt |
|---|---|---|---|---|---|---|---|---|
| (1) | —CH₂CH₂CH₂CH₂— | | Br | 8 | Cl | 6 | H | 320–322° C. dec.(2HCl) |
| (2) | H | —CF₃ | Br | 8 | Cl | 6 | H | — |
| (3) | H | o—Cl—C₆H₄— | Br | 8 | Cl | 6 | H | — |
| (4) | △ | —C₂H₅ | Br | 8 | Cl | 6 | —C₂H₅ | — |
| (5) | H | H | Cl | 5 | H | — | H | 236–236.5° C. (HOOC—⫝̸—COOH .½H₂O) |

TABLE III-continued

| Cpd. No. | $R^1$ | $R^2$ | X | $n_{xp}$* | Y | $n_y$** | $R^3$ | m.p. of salt |
|---|---|---|---|---|---|---|---|---|
| (6) | H | H | Br/Cl | 8 | H | — | H | 254–256° C. (2HCl . H$_2$O) |
| (7) | —CH$_3$ | H | Br | 8 | H | — | —CH$_2$— | — |
| (8) | H | H | Br | 8 | Cl | 6 | —CH$_3$ | 298 dec. (HCl . ½H$_2$O) |
| (9) | —CH$_2$— | H | Br | 8 | Cl | 6 | H | — |
| (11) | C$_6$H$_5$— | —CH$_3$ | Br/Cl | 8 | Cl | 6 | —C(=O)—CH$_3$ | — |
| (14) | p—CH$_3$C$_6$H$_4$— | —C$_3$H$_7$ | Br | 8 | —Cl | 6 | —C$_3$H$_7$ | — |
| (15) | H | m—CH$_3$O—C$_6$H$_4$— | Br | 8 | Cl | 6 |  | — |

$n_{xp}$* -position of either X or piperazinyl group
$n_y$** -position of Y

EXAMPLE 2

3-Chloro-8-(1-piperazinyl)imidazo[1,2-a]pyrazine hydrochloride

Step A: Preparation of a mixture of 3,8-dichloroimidazo[1,2-a]pyrazine and 8-bromo-3-chloro-imidazo[1,2-a]pyrazine A mixture of 1.6 g of 8-chloro and 8-bromoimidazo[1,2-a]pyrazines, and 1.4 g (10 mmol) of N-chloro-succinimide in 20 ml of chloroform is refluxed for 30 minutes. The reaction mixture is concentrated in vacuo and the residue is triturated with water to precipitate the crude product. It was filtered, dried in vacuo, sublimed, and then recrystallized from isopropanol to give a mixture of 3,8-dichloroimidazo[1,2-a]pyrazine and 8-bromo-8-chloroimidazo[1,2-a]pyrazine, m.p. 119°–122° C.

Employing the procedure substantially as described in Example 2, Step A, but substituting for the starting material used therein, an equimolecular amount of each of 6-chloroimidazo[1,2-a]pyrazine and 8-bromo-6-chloroimidazo[1,2-a]pyrazine, there is produced respectively 3,6-dichloroimidazo[1,2-a]pyrazine (m.p. 115°–116° C.) and 8-bromo-3,6-dichloroimidazo[1,2-a]pyrazine (m.p. 100°–101° C.).

Step B: Preparation of 3-chloro-8-(1-piperazinyl)imidazo[1,2-a]pyrazine

To a solution of the mixture of 3,8-dichloroimidazo[1,2-a]pyrazine and 8-bromo-3-chloroimidazo[1,2-a]pyrazine obtained above in 25 ml of acetonitrile is added an excess amount of piperazine (5 g). After refluxing and isolation in essentially the same manner as Example 1, Step B, 3-chloro-8-(1-piperazinyl)-imidazo[1,2-a]pyrazine hydrochloride salt is obtained with m.p. >300° C. dec.

Employing the procedure substantially as described in Example 2, Step B, but substituting for the starting material used therein an equimolecular amount of each of 3,6-dichloroimidazo[1,2-a]pyrazine and 8-bromo-3,6-dichloroimidazo[1,2-a]pyrazine, there is produced respectively: 3-chloro-6-(1-piperazinyl)imidazo[1,2-a]pyrazine. HCl.½ H$_2$O (m.p. >300° C.); and 3,6-dichloro-8-(1-piperazinyl)imidazo[1,2-a]pyrazine.HCl (m.p. >350° C.).

EXAMPLE 3

3-Methyl-8-(1-piperazinyl)imidazo[1,2-a]pyrazine hydrochloride

Step A: Preparation of 3-chloro-2-(2-hydroxypropan-1-amino)pyrazine

A mixture of 2,3-dichloropyrazine (25 g, 0.17 mole) and 2-hydroxy-1-propaneamine (25 g) in dioxane (100 ml) is refluxed 7 hours under nitrogen and the solvent evaporated under vacuum. The residue is partitioned between chloroform and water and the chloroform washed with water, dried over sodium sulfate, filtered and concentrated under vacuum to give crude 3-chloro-2-(2-hydroxypropan-1-amino)pyrazine as an oil.

Step B: Preparation of 3-chloro-2-(2-oxo-1-propanamino)pyrazine

To a solution of 28 g (0.15 mole) of 3-chloro-2-(2-hydroxy-1-propanamino)pyrazine in 100 ml triethylamine and 100 ml dimethylsufoxide is treated with 30 g (0.22 mole) trimethylamine sulfur trioxide complex with stirring for 20 hours at room temperature. The mixture is treated with 300 g ice and extracted with toluene. The toluene extract is washed with water, dried over sodium sulfate, filtered and concentrated under vacuum to give 25.5 g of the title compound as an oil. Recrystallization of a sample of crude produce from isopropanol give pure 3-chloro-2-(2-oxo-1-propanamino)pyrazine, m.p. 62°–62.5° C.

Step C: Preparation of 8-chloro-3-methylimidazo[1,2-a]pyrazine

A 2.67 g (0.01 mol) sample of 3-chloro-2-(2-oxo-1-propanamino)pyrazine is dissolved in 10 ml of trifluoroacetic anhydride under nitrogen and after the exothermic reaction subsides, the mixture is concentrated under vacuum. The residue is partitioned between chloroform and aqueous sodium bicarbonate, and the chloroform extract dried over sodium sulfate, filtered and concentrated under vacuum to give the solid 8-chloro-3-methylimidazo[1,2-a]pyrazine.

Step D: Preparation of 3-methyl-8-(1-piperazinyl)imidazo[1,2-a]hydrochloride

8-Chloro-3-methylimidazo[1,2-a]pyrazine is reacted with piperazine according to the procedure of Example 1, Step B, to give 3-methyl-8-(1-piperazinyl- )imidazo[1,2-a]hydrochloride after reaction with ethanolic hydrogen chloride.

EXAMPLE 4

3-Methyl-8-(1-piperazinyl)-2-(N-piperidinylmethyl)imidazo[1,2-a]pyrazine hydrochloride

Step A: Preparation of 3-chloro-2-(1-piperidino-3-oxo-2-butanamino)pyrazine hydrochloride A mixture of 3-chloro-2-(2-oxo-1-propanamino)pyrazine (1.86 g, 0.010 mol), piperidine hydrochloride (1.22 g, 0.10 mol) and paraformaldehyde (0.75 g) in 3 ml ethanol containing 1 drop of concentrated aqueous hydrochloric acid is refluxed 18 hours under nitrogen, cooled, diluted with isopropanol and treated with 1 ml of 8 N ethanolic hydrogen chloride. The crude product crystallizes to give 1.2 g of 3-chloro-2-(1-piperidino-3-oxo-2-butanamino)pyrazine hydrochloride, m.p. 183°–184° C.

Step B: Preparation of 8-chloro-3-methyl-2-(N-piperidinomethyl)imidazo[1,2-a]pyrazine hydrochloride A slurry of 3-chloro-2-(1-piperidino-3-oxo-2-butanamino)pyrazine hydrochloride (1.0 g, 0.0031 mole) in 2 ml trifluoroacetic acid is treated with 0.5 ml trifluoroacetic anhydride and the mixture refluxed 1.5 hours on the steam bath. The mixture is cooled, partitioned between chloroform and saturated aqueous sodium carbonate. The chloroform extract is dried over sodium sulfate, filtered and concentrated under vacuum to the crude solid base which is dissolved in hot ethanol. Addition of ethanolic hydrogen chloride precipitates 0.8 g of 8-chloro-3-methyl-2-(N-piperidinomethyl)imidazo[1,2-a]pyrazine, m.p. 290–310 dec.

Step C: Preparation of 3-methyl-8-(1-piperazinyl)-2-(N-piperidinylmethyl)imidazo[1,2-a]pyrazine hydrochloride 2-(N-piperidinomethyl)-3-methyl-8-chloroimidazo[1,2-a]pyrazine is reacted with piperazine according to the procedure of Example 1, Step B, 3-methyl-8-(1-piperazinyl)-2-(N-piperidinylmethyl)imidazo[1,2-a]pyrazine which is crystallized as its dihydrochloride from ethanolic hydrogen chloride.

EXAMPLE 5

8-(1-Piperazinyl)-6-trifluoromethyl-3-methylimidazo[1,2-a]pyrazine hydrochloride

Step A: Preparation of 3-chloro-2-(2-propyn-1-ylamino)pyrazine-5-carboxylic acid A mixture of 2,3-dichloropyrazine-5-carboxylic acid (19.3 g, 0.100 mole) and 3-amino-1-propyne (1.10 g, 0.20 mole) in 100 ml dioxane is refluxed for 24 hours, cooled and concentrated under vacuum. The residue is partitioned between aqueous sodium bicarbonate and chloroform and the aqueous extract neutralized with acetic acid to give a precipitate of 3-chloro-2-(2-propyn-1-ylamino)pyrazine-5-carboxylic acid.

Step B: Preparation of 8-chloro-3-methylimidazo[1,2-a]pyrazine-6-carboxylic acid 3-Chloro-2-(2-propyn-1-ylamino)pyrazine-5-carboxylic acid is dissolved in 100 ml trifluoroacetic acid containing 1 g of mercuric oxide and the mixture is heated 4 hours on the steam bath and concentrated under vacuum. The residue is dissolved in aqueous sodium bicarbonate and 8-chloro-3-methylimidazo[1,2-a]pyrazine-6-carboxylic acid precipitated with acetic acid by adjusting the pH to approximately 7.

Step C: Preparation of mixture of 8-fluoro- and 8-chloro-3-methyl-6-trifluoromethylimidazo[1,2-a]pyrazine 8-Chloro-3-methylimidazo[1,2-a]pyrazine-6-carboxylic acid is dissolved in a mixture of 12 ml hydrogen fluoride and 27 g sulfur tetrafluoride and one drop of mercury in a stainless steel pressure tube reactor and the mixture is heated 6 hours at 150° C. under pressure with shaking. The mixture is cooled and vented, quenched in ice water, and the aqueous mixture adjusted to pH 7 with sodium hydroxide and extracted with methylene chloride. Concentration of the methylene chloride after drying over sodium sulfate gives the crude mixture of 8-fluoro- and 8-chloro-3-methyl-6-trifluoromethylimidazo[1,2-a]pyrazine.

Step D: Preparation of 3-methyl-8-(1-piperazinyl)-6-trifluoromethylimidazo[1,2-a]pyrazine hydrochloride The mixture of 8-fluoro- and 8-chloro-3-methyl-6-trifluoromethylimidazo[1,2-a]pyrazine is reacted with piperazine as in Example 1, Step A to give 3-methyl-8-(1-piperazinyl)-6-trifluoromethylimidazo[1,2-a]pyrazine, isolated as the hydrochloride from aqueous ethanolic hydrogen chloride.

Employing the procedure substantially as described in Example 5, Step D, but substituting for the starting materials used therein an equimolecular amount of 8-chloro-3-methylimidazo[1,2-a]pyrazine-6-carboxylic acid, there is produced 3-methyl-8-(1-piperazinyl)imidazo[1,2-a]pyrazine-6-carboxylic acid.

EXAMPLE 6

6-(1-Piperazinyl)-3-trifluoromethylthioimidazo[1,2-a]pyrazine hydrochloride

Step A: Preparation of 6-chloro-3-trifluoromethylthioimidazo[1,2-a]pyrazine

A solution of 6-chloroimidazo[1,2-a]pyrazine (3.07 g, 0.020 mol) in acetonitrile (50 ml) containing 1.01 g (0.010 mol) of triethylamine is treated with a stream of trifluoromethanesulfenyl chloride gas at 25° C. under nitrogen. After 1 hour the solution is flushed with nitrogen, concentrated under vacuum, and the residue partitioned between water-chloroform. The chloroform extract is dried over sodium sulfate, filtered and concentrated under vacuum to give crude 6-chloro-3-trifluoromethylthioimidazo[1,2-a]pyrazine which is purified by fractional sublimation.

Employing the procedure substantially as described in Example 6, Step A, but substituting for trifluoromethanesulfenyl chloride used therein an equimolecular amount of 1-butyl sulfenyl chloride, there is produced 3-(1-butylthio)-6-chloroimidazo[1,2-a]pyrazine.

Step B: Preparation of 6-(1-piperazinyl)-3-trifluoromethylthioimidazo[1,2-a]pyrazine 6-Chloro-3-trifluoromethylthioimidazo[1,2-a]pyrazine from Step A is reacted with piperazine (2 g) in efluxing acetonitrile for 24 hours. The mixture is cooled, concentrated under vacuum, and the esidue partitioned between dilute sodium hydroxide and chloroform. The chloroform extract is dried over sodium sulfate, filtered and concentrated under vacuum to the crude base which is purified by chromatography on silica gel and converted to 6-(1-piperazinyl)-3-trifluoromethylthioimidazo[1,2-a]pyrazine hydrochloride with ethanolic hydrogen chloride.

Employing the procedure substantially as described in Example 6, Step B, but substituting for the starting material used therein an equimolecular amount of 3-(1-butylthio)-6-chloroimidazo[1,2-a]pyrazine, there is produced 3-(1-butylthio-6-(1-piperaziyl)imidazo[1,2-a]pyrazine.

EXAMPLE 7

3-(N,N-dimethylsulfamoyl)-6-(1-piperazinyl)imidazo[1,2-a]pyrazine hydrochloride

Step A: Preparation of 6-chloro-3-(N,N-dimethylsulfamoyl)imidazo[1,2-a]pyrazine

6-Chloroimidazo[1,2-a]pyrazine (3.07 g, 0.020 mole) is added in portions with stirring to 20 ml chlorosulfonic acid, and the mixture heated 2 hours at 100° C. and then cooled to room temperature. Thionyl chloride (2 g) is added and the mixture reheated to 100° C. for 2 hours. After cooling to room temperature, the mixture is quenched on crushed ice and extracted with ether. The ether layer is dried over sodium sulfate, filtered and concentrated under vacuum to give an oil which is stirred with a mixture of crushed ice and aqueous dimethylamine for one hour. The crude 6-chloro-3-(N,N-dimethylsulfamoyl)imidazo[1,2-a]pyrazine is collected by filtration.

Step B: Preparation of 3-(N,N-dimethylsulfamoyl)-6-(1-piperazinyl)imidazo[1,2-a]pyrazine hydrochloride The crude product from Step A is reacted with piperazine (2 g) in refluxing acetonitrile for 18 hours and the mixture cooled and concentrated under vacuum, and the residue partitioned between dilute sodium hydroxide and chloroform. The chloroform extract is dried over sodium sulfate, filtered and concentrated under vacuum to a residue which is purified by chromatography on silica gel and crystallized from ethanolic hydrogen chloride to give 3-(N,N-dimethylsulfamoyl)-6-(1-piperazinyl)imidazo[1,2-a]pyrazine hydrochloride.

EXAMPLE 8

| Preparation of Capsule Formulation | |
|---|---|
| Ingredient | Milligrams per Capsule |
| 3-Chloro-8-(1-piperazinyl)imidazo[1,2-a]pyrazine | 6 |
| Starch | 87 |
| Magnesium stearate | 7 |
| Total weight | 100 mg. |

The active ingredient, starch and magnesium stearate are blended together. The mixture is used to fill hard shell capsules of a suitable size at a fill weight of 100 mg per capsule.

EXAMPLE 9

| Preparation of Tablet Formulation | |
|---|---|
| Ingredient | Milligrams per Tablet |
| 8-(1-piperazinyl)imidazopyrazine dihydrochloride monohydrate | 12 |
| Lactose | 200 |
| Corn starch (for mix) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of active ingredient.

What is claimed is:

1. A compound of the structural formula:

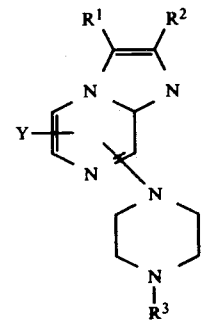

or a pharmaceutically acceptable salt thereof, wherein: the piperazinyl group

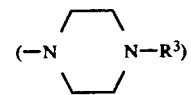

and Y are at positions 5, 6 or 8;
$R^1$ and $R^2$ independently ar
 (a) hydrogen;
 (b) lower alkyl;
 (c) lower cycloalkyl;
 (d) lower alkylthio;
 (e) halo;
 (f) —$CF_3$;
 (g) $CF_3S$—;
 (h) $C_6H_5$—;
 (i) phenyl-substituted by halogen;
 (j) phenyl-substituted by $C_{1-3}$ alkyl;
 (k) phenyl-substituted by $C_{1-3}$ alkoxy;
 (l)

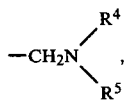

wherein $R^4$ is hydrogen or $C_{1-6}$ alkyl; $R^5$ is $C_{1-6}$ alkyl; or $R^4$ and $R^5$ taken together form with the nitrogen atom to which they are attached, a piperidino group;

(m)

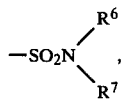

wherein $R^6$ and $R^7$ are independently hydrogen, $C_{1-3}$ alkyl, or phenyl; or
$R^1$ and $R^2$ joined together form $-CH_2CH_2CH_2-$ or $-CH_2CH_2CH_2CH_2-$;
$R^3$ is
  (a) hydrogen;
  (b) lower alkyl;
  (c) lower(cycloalkyl-alkyl);
  (d) lower cycloalkyl; or
  (e) lower alkanoyl;
Y is
  (a) hydrogen;
  (b) halo;
  (c) $-C\equiv N$;
  (d) $-CF_3$;
  (e) lower alkyl
  (f) lower alkoxy; or
  (g) $-COOH$.

2. The compound of claim 1 or a pharmaceutically acceptable salt thereof, wherein the piperazinyl group and Y are at position 6 or 8;
$R^1$ and $R^2$ are independently
  (a) hydrogen;
  (b) halo;
  (c) $CF_3$;
  (d) $CF_3S$;
  (e) $C_6H_5$;
  (f) phenyl-substituted by halogen;
  (g)

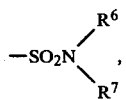

wherein $R^6$ and $R^7$ are independently hydrogen, $C_{1-3}$ alkyl, or phenyl;
(h)

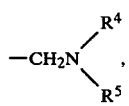

wherein $R^4$ is hydrogen or $C_{1-6}$ alkyl; $R^5$ is $C_{1-6}$ alkyl; or $R^4$ and $R^5$ taken together form with the nitrogen atom to which they are attached, a piperidino group; or $R^1$ and $R^2$ are joined together form $-CH_2CH_2CH_2-$ or $-CH_2CH_2CH_2CH_2-$;
$R^3$ is
  (a) hydrogen;
  (b) $C_{1-3}$ alkyl;
  (c) $C_{1-3}$ alkanoyl;
  (d) cyclopropylmethyl; or
  (e) cyclopropyl or cyclohexyl; and
Y is
  (a) hydrogen;
  (b) Cl, F, Br, or I;
  (c) $-C\equiv N$
  (d) $-CF_3$; or
  (e) $CH_3O-$.

3. The compound of claim 1 or a pharmaceutically acceptable salt thereof, wherein the piperazinyl group is at position 8; and Y is at position 6;
$R^1$ and $R^2$ are independently
  (a) hydrogen;
  (b) Cl, Br or F;
  (c) $CF_3$;
  (d) $CF_3S$;
  (e) $o-Cl-C_6H_4-$;
  (f) $-SO_2N(CH_3)_2$;
  (g)

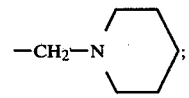

or
where $R^1$ and $R^2$ are joined together they form $-CH_2CH_2CH_2CH_2-$;
$R^3$ is
  (a) hydrogen;
  (b) $-CH_3$; or
  (c) cyclopropylmethyl; and
Y is
  (a) hydrogen; or
  (b) Cl, F, or Br.

4. The compound of claim 1 or a pharmaceutically acceptable salt thereof, wherein the piperazinyl group is at position 8; and Y is at position 6;
$R^1$ and $R^2$ are independently
  (a) hydrogen; or
  (b) Cl;
$R^3$ is
  (a) hydrogen; or
  (b) $-CH_3$; and
Y is
  (a) hydrogen; or
  (b) Cl.

5. The compound of claim 1 which is 3-chloro-6-(1-piperazinyl)imidazol[1,2-a]pyrazine or a pharmaceutically acceptable salt thereof.

6. The compound of claim 1 which is 8-(1-piperazinyl)imidazo[1,2-a]pyrazine or a pharmaceutically acceptable salt thereof.

7. A method of decreasing appetite, which comprises the administration to a mammalian species in need of such treatment an effective amount of a compound of formula:

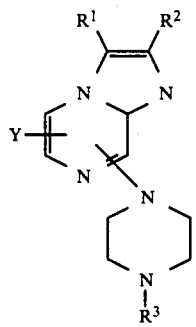

or a pharmaceutically acceptable salt thereof, wherein: the piperazinyl group

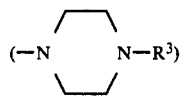

and Y are at positins 5, 6 or 8;
$R^1$ and $R^2$ independently are
(a) hydrogen;
(b) lower alkyl;
(c) lower cycloalkyl;
(d) lower alkylthio;
(e) halo;
(f) —$CF_3$;
(g) $CF_3S$—;
(h) $C_6H_5$—;
(i) phenyl-substituted by halogen;
(j) phenyl-substituted by $C_{1-3}$ alkyl;
(k) phenyl-substituted by $C_{1-3}$ alkoxy;
(l)

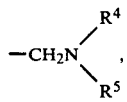

wherein $R^4$ is hydrogen or $C_{1-6}$ alkyl; $R^5$ is $C_{1-6}$ alkyl; or $R^4$ and $R^5$ taken together form with the nitrogen atom to which they are attached, a piperidino group;
(m)

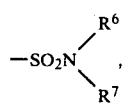

wherein $R^6$ and $R^7$ are independently hydrogen, $C_{1-3}$ alkyl, or phenyl; or
$R^1$ and $R^2$ joined together form —$CH_2CH_2CH_2$— or —$CH_2CH_2CH_2CH_2$—;
$R^3$ is
(a) hydrogen;
(b) lower alkyl;
(c) lower(cycloalkyl-alkyl);
(d) lower cycloalkyl; or
(e) lower alkanoyl;
Y is
(a) hydrogen;
(b) halo;

(c) —C≡N;
(d) —$CF_3$;
(e) lower alkyl;
(f) lower alkoxy; or
(g) —COOH.

8. A pharmaceutical composition for decreasing appetite, in a mammalian species comprising a pharmaceutical carrier and an effective amount of a compound of formula:

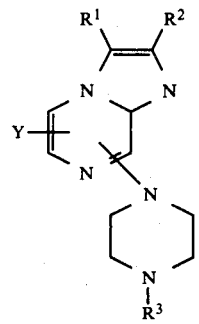

or a pharmaceutically acceptable salt thereof, wherein: the piperazinyl group

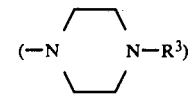

and Y are at positions 5, 6 or 8;
$R^1$ and $R^2$ independently are
(a) hydrogen;
(b) lower alkyl;
(c) lower cycloalkyl;
(d) lower alkylthio;
(e) halo;
(f) —$CF_3$;
(g) $CF_3S$—;
(h) $C_6H_5$—;
(i) phenyl-substituted by halogen;
(j) phenyl-substituted by $C_{1-3}$ alkyl;
(k) phenyl-substituted by $C_{1-3}$ alkoxy;
(l)

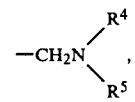

wherein $R^4$ is hydrogen or $C_{1-6}$ alkyl; $R^5$ is $C_{1-6}$ alkyl; or $R^4$ and $R^5$ taken together form with the nitrogen atom to which they are attached, a 5 or 6 membered heterocycle;
(m)

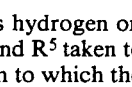

wherein $R^6$ and $R^7$ are independently hydrogen, $C_{1-3}$ alkyl, or phenyl; or
$R^1$ and $R^2$ joined together form —$CH_2CH_2CH_2$— or —$CH_2CH_2CH_2CH_2$—;

$R^3$ is
- (a) hydrogen;
- (b) lower alkyl;
- (c) lower(cycloalkyl-alkyl);
- (d) lower cycloalkyl; or
- (e) lower alkanoyl;

Y is
- (a) hydrogen;
- (b) halo;
- (c) —C≡N
- (d) —CF$_3$;
- (e) lower alkyl;
- (f) lower alkoxy; or
- (g) —COOH.

9. The pharmaceutical composition of claim 8 wherein the compound is that of claim 2, 3, 4, 5 or 6.

* * * * *